US012737837B2

(12) United States Patent
Sarti et al.

(10) Patent No.: US 12,737,837 B2
(45) Date of Patent: Sep. 15, 2026

(54) IMAGE PROCESSING METHOD TO GENERATE A PANORAMIC IMAGE

(71) Applicant: See Through S.R.L., Brusaporto (IT)

(72) Inventors: Cristina Sarti, Frankfurt am Main (DE); Claudio Landi, Milan (IT); Klaus Maier, Salzburg (AT)

(73) Assignee: See Through S.R.L., Brusaporto (IT)

( * ) Notice: Subject to any disclaimer, the term of this patent is extended or adjusted under 35 U.S.C. 154(b) by 375 days.

(21) Appl. No.: 17/852,029

(22) Filed: Jun. 28, 2022

(65) Prior Publication Data

US 2023/0009661 A1 Jan. 12, 2023

(30) Foreign Application Priority Data

Jul. 9, 2021 (EP) .................................... 21184649

(51) Int. Cl.
*G06T 3/4038* (2024.01)
*A61B 6/51* (2024.01)
(Continued)

(52) U.S. Cl.
CPC .............. *G06T 3/4038* (2013.01); *A61B 6/51* (2024.01); *G06T 3/10* (2024.01); *G06T 7/0012* (2013.01);
(Continued)

(58) Field of Classification Search
None
See application file for complete search history.

(56) References Cited

U.S. PATENT DOCUMENTS 6,075,905 A 6/2000 Herman
10,049,467 B2 * 8/2018 Im .......................... A61B 6/466
2015/0073276 A1 * 3/2015 Napolitano .......... A61B 8/4483 600/447
2022/0022827 A1 * 1/2022 Maur ....................... A61B 6/51

FOREIGN PATENT DOCUMENTS

EP 2852153 A1 * 3/2015 ........... G06T 11/003
EP 3685752 A1 * 7/2020 ............... A61B 6/14
JP 2010-148676 A 7/2010
JP 4844886 B2 * 12/2011 ............... A61B 6/14
KR 101389841 B1 4/2014

OTHER PUBLICATIONS

Ogawa, K., Langlais, R. P., McDavid, W. D., Noujeim, M., Seki, K., Okano, T., Yamakawa, T., & Sue, T. (2010). Development of a new dental panoramic radiographic system based on a tomosynthesis method. Dento maxillo facial radiology, 39(1), 47-53. https://doi.org/10.1259/dmfr/12999660.*

(Continued)

*Primary Examiner* — Andrew W Bee
*Assistant Examiner* — Christine Zhao
(74) *Attorney, Agent, or Firm* — Wood, Phillips, Katz, Clark & Mortimer

(57) ABSTRACT

An image processing method to provide a final panoramic image of at least a portion of a head of a patient, wherein a plurality of different provisional panoramic images are calculated from captured frame data sets through the variation of a reconstruction parameter; the provisional panoramic images are scanned for recognizable structures; the imaging quality of the recognizable structures is determined; the variation of the at least one reconstruction parameter for the calculation of different provisional panoramic images of those frame data sets which have recognizable structures with the highest imaging quality is determined; and with reference to the determined variation of the reconstruction (Continued)

parameter of step a final panoramic image is calculated. A computer-readable storage medium comprising instructions which cause a computer to perform the method and an imaging system having such a storage medium are also described.

19 Claims, 3 Drawing Sheets

(51) Int. Cl.
*G06T 3/10* (2024.01)
*G06T 7/00* (2017.01)

(52) U.S. Cl.
CPC ............... *G06T 2207/10116* (2013.01); *G06T 2207/20212* (2013.01); *G06T 2207/30036* (2013.01); *G06T 2207/30168* (2013.01)

(56) References Cited

OTHER PUBLICATIONS

Dobbins, J. T., 3rd, & Godfrey, D. J. (2003). Digital x-ray tomosynthesis: current state of the art and clinical potential. Physics in medicine and biology, 48(19), R65-R106. https://doi.org/10.1088/0031-9155/48/19/r01.*

European Search Report issued Dec. 2, 2021, in European Patent Application No. EP 21 18 4649.

Lira, Pedro H. M. et al., "Panoramic Dental X-Ray Image Segmentation and Feature Extraction", Proceedings of the V Workshop On Computing Vision, Jan. 1, 2009, pp. 1-6, Sao Paulo, Brazil.

Anonymous, "Rate", The IEEE Standard Dictionary of Electrical and Electronics Terms, Jan. 1, 1996, 6th Ed., p. 866.

* cited by examiner 1
3
4
11
7
2
8
12
6
9
10
5
1
2
10
9

IMAGE PROCESSING METHOD TO GENERATE A PANORAMIC IMAGE

CROSS REFERENCE TO RELATED APPLICATION

The present application claims priority from pending European Patent Application No. EP 21184649.8, filed Jul. 9, 2021, which is incorporated herein by reference.

FIELD

The present invention relates to a medical or dental image processing method to provide image data for creation of a panoramic image (2D panoramic image) of at least a portion of a head, in particular a portion of an oral region of a head of a patient. The method is in particular configured to provide panoramic images with improved representation of the geometry of anatomical structures shown on the panoramic image. The present invention also relates to a computer program and a medical or dental imaging system which are configured to implement said image processing method.

DESCRIPTION OF PRIOR ART

For diagnosis and treatment, it is necessary to provide images of body parts or anatomic regions, in particular the head, the oral cavity, the jaw or portions thereof. To this purpose imaging devices, for example x-ray devices comprising an x-ray source and an x-ray sensor are provided. Before an image can be recorded a patient has to be placed in a target position of such an imaging device. Then, a plurality of single images or frame data sets of the body part is captured under different angles with the x-ray source and the x-ray sensor moving or rotating around the patient's body part to be imaged. Next, relying on computational processing, calculations and/or an algorithm a 2D panoramic image of the scanned anatomic region is reconstructed out of the single images.

For the whole length of the scan the patient head is expected to stay in the target position. However, in many cases, this cannot be guaranteed. Deviations from the target position can occur due to several factors, for example, because of poor positioning of the patient before the start of the scan, motion of the patient during the scan, deviation of the x-ray source or x-ray sensor from its determined path of rotation, incorrect scan settings by the user, etc.

Deviations from the target position, for whatever reason, finally result in 2D panoramic images with minor image quality, in particular with poor representation of the geometry of at least some of the anatomical structures, in particular of teeth, shown on the panoramic image. For example, geometrical distortions of anatomical structures may occur and/or relevant anatomic parts are represented with the wrong proportions. Also features of at least some of the anatomical structures, in particular of teeth, shown on the panoramic image, may overlap, wrong orientations of the anatomical structures, e.g. tooth roots, may occur and/or due to blurriness, the visibility of relevant anatomical structures is impaired. As a result, diagnosis based on such 2D panoramic images having poor quality can be very hard or impossible, the risk of overlooking an important feature rises or, in the worst case, a misdiagnosis could be made.

A medical or dental image processing method which aims to provide an improved final 2D panoramic image is known for example from patent application JP 2010-148676 A, in which first an impression of the dentition of a patient is made and images of the impression are captured by a camera, then a body portion of the patient is x-rayed and a panoramic image of the body portion is calculated and finally relying on the shape of the patient impression, a user can modify the shape of a reconstruction curve to globally or locally optimize the final panoramic image.

A disadvantage of the method according to JP 2010-148676 A is the requirement of an impression of the dentition of a patient and the capturing of the impression by a camera

SUMMARY

It is thus an object to provide an alternative medical or dental image processing method for creation of a 2D panoramic image, which in particular overcomes the disadvantages of the prior art. The method shall in particular provide panoramic images with improved representation of the geometry of anatomical structures shown on the panoramic image, wherein the improved representation of the geometry of anatomical structures shall preferably be based on the individual physical properties of each patient without the need for previously taking and capturing an impression of the dentition of the patient.

These objects are achieved by an image processing method, in particular a computer implemented image processing method, a computer program product or computer-readable storage medium, and a medical or dental imaging system as described and summarized below.

The (computer implemented) image processing method is configured to provide a final panoramic image of at least a portion of a head, in particular of a portion of an oral region of a head of a patient, wherein the image processing method comprises:

i. providing a plurality of frame data sets captured by a medical or dental imaging system having a radiation source and a radiation detector which move about the patient while taking the plurality of frame data sets;
ii. calculating from said plurality of frame data sets a plurality of provisional panoramic images which differ from one another due to the variation of at least one reconstruction parameter used during calculation of the plurality of provisional panoramic images (14);
iii. scanning the provisional panoramic images of said plurality of provisional panoramic images for recognizable structures;
iv. determining the imaging quality of the recognizable structures;
v. determining the variation of the at least one reconstruction parameter used in step (ii) for the calculation of the plurality of provisional panoramic images of those frame data sets which have recognizable structures with the highest imaging quality;
vi. calculating with reference to the determined variation of the at least one reconstruction parameter of step (v) a final panoramic image data set representing a final panoramic image; and
vii. displaying the final panoramic image represented by the final panoramic image data set.

As used herein, the term 'frame data set' means a single image or data of or for a single image captured by the medical or dental imaging system, for example an x-ray device. Further, as used here, the term panoramic image or final panoramic image means a 2D (final) panoramic image, in particular of at least a portion of an oral region of a patient, for example of at least one of a jaw, a plurality of teeth, a plurality of tooth roots, dental implants etc.

Advantageously, the method provides a final panoramic image with improved or corrected geometrical representation of structures which, due to deviations from the target position, have initially been captured with a minor quality. Thus, the method advantageously approaches a panoramic image captured in the target position in which structures are shown in an optimal geometrical or spatial arrangement.

Advantageously, the image processing method does not need a reference model, i.e. an impression of a dentition, for the creation of the final panoramic image, in particular a final panoramic image with improved representation of the geometry of anatomical structures shown on the final panoramic image. Rather, as will be described in detail below, the image processing method relies on the plurality of captured frame data sets of the respective patient and the plurality of different provisional panoramic images derived from this plurality of captured frame data sets. In particular, for the creation of the final panoramic image of a certain patient only frame data sets of this patient are used. Accordingly, the creation of the final panoramic image, i.e. the correction of the geometry of the anatomical structures displayed on the final panoramic image, is advantageously based or tailored on the individual properties of the respective patient.

Further, the image processing method relies on recognizable structures and the imaging quality of these recognizable structures, but advantageously the recognizable structures of the provisional panoramic images do not have to be attributed to the anatomy of the head, e.g. to anatomical structures like a front tooth, a molar, the palate, etc. Rather, for the instant image processing method it is sufficient to recognize parts of one or more structures or one or more entire structures of the provisional panoramic images without attributing them to actual anatomical structures, since there is no need to relate such a structure to a reference model. This in addition simplifies the correction of the geometry of the anatomical structures and thus the creation of the final panoramic image.

The patient may preferably be a human being or an animal. The at least one part of the head of the patient to be imaged by the medical or dental imaging system may comprise for example a forehead, a face, an oral cavity, a jaw, at least one tooth, a dental root canal, a nasal bone, or any other part of the head of the patient.

The medical or dental imaging system preferably comprises an x-ray device. The medical or dental imaging system preferably comprises a supporting structure, a rotation unit rotatably coupled to the supporting structure, a chin rest and/or bite block for the patient, a computer configured to perform at least portions of the image processing method and/or configured to provide the final panoramic image data set and a display device to display the final panoramic image based on the final panoramic image data set provided by the computer.

Preferably, the rotation unit comprises an x-ray source for the emission of x-rays towards the head or the at least one part of the head to be imaged and an x-ray detector which is configured to receive at least a portion of the x-rays emitted by the x-ray source, in particular the x-rays which have penetrated the head or head part to be imaged. The rotation unit comprises a cantilever or a rotating arm having two opposing end sections, wherein the x-ray source is attached to one of these respective end sections and the x-ray detector is attached to the other of these respective end sections. The radiation or x-ray source and the radiation or x-ray detector move about the patient, the x-ray source emits x-rays and the x-ray detector receives at least a portion of these x-rays while taking the plurality of frame data sets. Since such medical or dental imaging systems are well known from the prior art, no further description is given.

The chin rest and/or bite block defines or comprises the target position to which the calculation rules, metrics and/or algorithms with their specific calculation, correction and/or reconstruction parameters used for the calculation of the final panoramic image refer to or depend on. Since, as described in detail above, deviations from the target position can occur the instant (computer implemented) image processing method is needed to provide an improved or corrected final panoramic image with improved representation of the geometry of anatomical structures shown on the final panoramic image.

Accordingly, the first step of the method comprises providing a plurality of frame data sets captured by the medical or dental imaging system as described above. The plurality of frame data sets captured may comprise without any limitation to a specific number or range for example hundreds or some thousand single frames data sets. The plurality of frame data sets is preferably stored in a memory of the medical or dental imaging system, in particular in the computer. Preferably frame data sets which have been captured immediately one after the other (i.e. without another frame data set in between) partially comprise same data or partially image or record same structures. Preferably a plurality of frame data sets which have been captured consecutively partially comprise same data or partially image or record same structures, wherein the more distant two frame data sets or frames are, the less is the amount of same data, images or structures they comprise.

Next, a plurality of provisional panoramic images is calculated by calculation rules, metrics and/or algorithms, preferably stored in the computer, from said plurality of frame data sets. A provisional panoramic image may comprise all frame data sets captured by the imaging system or may comprise a subset of these frame data sets. A provisional panoramic image may thus for example represent either the whole mandibular arch or jaw or only a part of it. The plurality of calculated provisional panoramic images may comprise without any limitation to a specific number or range for example 2 to 20, or more than 20.

In order to calculate the provisional panoramic images, the frame data sets are arranged in the order they were captured and in an overlapping manner, since, as described above, frame data sets which have been captured immediately one after the other partially comprise same data or partially image or record same structures. Generally, the rate of overlap is determined by given parameters, like the target position, parameters of the medical or dental imaging system, etc., wherein these given parameters are reflected by or define the calculation rules, metrics and/or algorithms for the calculation of the provisional panoramic images.

Preferably, arranging the frame data sets in an overlapping manner may comprise that gray values of pixels of the different frame data sets are summed up in overlapping areas and the average of the gray values is calculated, resulting in gray values of a provisional panoramic image.

In order to calculate the plurality of provisional panoramic images which differ from one another at least one reconstruction parameter is varied during calculation of the provisional panoramic images. The at least one reconstruction parameter may comprise for example at least one of: a rate of overlap of the frame data sets; a rate of scaling of the frame data sets; a pixel shift; or similar or other known parameters. Preferably for the calculation of each provisional panoramic image of the plurality of provisional panoramic images the at least one reconstruction parameter is varied, so that in particular each provisional panoramic image of the plurality of provisional panoramic images has its unique or specific variation of the at least one reconstruction parameter. The calculation of the plurality of provisional panoramic images in particular and advantageously simulates different positions of a patient or angles of view on a patient.

Preferably, the variation of the at least one reconstruction parameter for the calculation of a provisional panoramic image may comprise an increase or a decrease of the at least one reconstruction parameter.

Preferably, the variation of the rate of overlap for the calculation of a provisional panoramic image comprises the variation of overlap or moving of the frame data sets along a single axis, in particular along a horizontal direction or abscissa of the frame data sets. Preferably, the variation of the rate of overlap for the calculation of a single provisional panoramic image of the plurality of provisional panoramic images is the same for all frame data sets used for the calculation of this single provisional panoramic image.

Preferably, the variation of the rate of scaling for the calculation of a provisional panoramic image may comprise an increase or a decrease of the rate of scaling, i.e. an upscaling or a downscaling. Preferably, the variation of the rate of scaling for the calculation of a provisional panoramic image comprises the scaling of the frame data sets along a single axis, in particular along a horizontal direction or abscissa of the frame data sets. Alternatively, it is also conceivable that the frame data sets are scaled along two axes, i.e. in a horizontal direction or abscissa and a vertical direction or ordinate of the frame data sets. Preferably, the variation of the rate of scaling for the calculation of a single provisional panoramic image of the plurality of provisional panoramic images is the same for all frame data sets used for the calculation of this single provisional panoramic image.

Preferably, one provisional panoramic image may be calculated with a value or variation of the at least one reconstruction parameter according to the target position or determined by the given parameters. Accordingly, the plurality of provisional panoramic images may comprise one provisional panoramic image which corresponds to the target position.

Accordingly, for the calculation of n different provisional panoramic images (which together form the plurality of provisional panoramic images) n variations of the at least one reconstruction parameter or n different values of the reconstruction parameter are applied to the captured frame data sets. It is also conceivable that for the calculation of at least one provisional panoramic image of the plurality of provisional panoramic images more than one reconstruction parameter is varied and applied to the captured frame data sets to calculate this at least one provisional panoramic image.

Thus, due to the variation of the at least one reconstruction parameter a plurality of provisional panoramic images having different properties and/or defining different spatial or geometrical patient positions are created. The different properties and/or positions may comprise for example at least one of spatial positioning, proportions or dimensions of structures represented on the provisional panoramic images.

Preferably, the rate of variation of the at least one reconstruction parameter, i.e. distances between different values of the at least one reconstruction parameter used for the calculation of different provisional panoramic images, are pre-set and cannot be altered or selected by a user. Alternatively, a user can at least within certain limits directly or indirectly select or set the rate of variation of the at least one reconstruction parameter. For example, a user can select different head sizes, e.g. small—medium—large, depending on the head size of the patient and/or on the dimension of the portion of the head to be imaged, and hence the rate of variation of the at least one reconstruction parameter is matched by the computer of the medical or dental imaging system to the selected head size. Accordingly, the medical or dental imaging system comprises a setting device for a user to set or select directly or indirectly the rate of variation of the at least one reconstruction parameter.

After the calculation of the plurality of provisional panoramic images the provisional panoramic images are scanned for recognizable structures. As already described above, the recognizable structures of the provisional panoramic images do not have to be attributed to the anatomy, i.e. to anatomical structures of the head. Rather, it is sufficient to recognize parts of one or more structures or one or more entire structures of the provisional panoramic images without attributing them to actual anatomical structures. The recognizable structures may comprise for example at least a portion of one or more of the following structures: an anatomical structure, in particular a tooth, a tooth root, a palate, a jaw bone, a bone of the skull, a vertebra; an artificial structure, in particular a prothesis, a crown, an implant, a dental filling, a retainer.

Well known methods for digital image processing can be used for the scanning for recognizable structures, which for example use pattern recognition, in particular statistical pattern recognition, classification, feature extraction etc. It is also conceivable that a trained artificial neural network performs the digital image processing.

Further, the imaging quality of the scanned recognizable structures of the provisional panoramic images is determined. Determining the imaging quality preferably comprises digital image data processing of those frame data sets which comprise scanned recognizable structures.

Well known methods for digital image processing, in particular statistical methods, can be used to determine the imaging quality of the scanned recognizable structures. These methods may comprise for example a frequency analysis and/or a grey value distribution analysis and/or brightness distribution analysis, in particular of the pixels of the frame data sets comprising recognizable structures. Alternatively or in addition, a trained artificial neural network performs the determination of the imaging quality of the scanned recognizable structures by using these and/or other methods.

With respect to the determination of the imaging quality in particular geometrical parameters are considered, for example spatial positioning, proportions or dimensions of structures and/or of anatomical features represented on the provisional panoramic images.

Since, as described above, a plurality of different provisional panoramic images has been calculated, a particular recognizable structure is present on at least some, preferably all of these different provisional panoramic images. According to the previous step, the imaging quality of this particular recognizable structure represented on the different provisional panoramic images has been determined. In a next step, the imaging qualities of the particular recognizable structure present on different provisional panoramic images are compared and the provisional panoramic image having the particular recognizable structure with the highest imaging quality is determined. Alternatively or in addition, the frame data sets representing the particular recognizable structure with the highest imaging quality are determined.

Especially preferred, this 'determination of the highest imaging quality step' is performed for a plurality of different recognizable structures present on at least some, preferably all of these different provisional panoramic images.

According to a preferred embodiment, the provisional panoramic images are divided into a plurality of regions of interest (ROIs) or sections, wherein the number of the plurality of ROIs or sections preferably is identical for each provisional panoramic image. The plurality of identical ROIs or sections may comprise without any limitation to a specific number 2-15 sections or ROIs per provisional panoramic image, or more than 15. As will be described in the following, the division of the provisional panoramic images into identical sections or ROIs simplifies and thus accelerates in an advantageous manner the calculation of the final panoramic image data set.

The sections or ROIs of the plurality of identical sections or ROIs may have the same dimensions, which advantageously simplifies the method. Alternatively, the sections or ROIs of the plurality of identical sections or ROIs may have different dimensions, wherein in particular the width (relative to a horizontal direction or abscissa of the provisional panoramic images) of the sections/ROIs is variable, while the height (relative to a vertical direction or ordinate of the provisional panoramic images) is constant. Of course, variation only of the height or of the height and the width are also possible. Sections or ROIs having different dimensions advantageously result in a more accurate calculation of the final panoramic image. For example, sections or ROIs at the peripheries of the provisional panoramic images may have a smaller width and sections/ROIs at the center of the provisional panoramic images may have a wider width. Preferably, the sections or ROIs may have the same or different shapes, for example a rectangular or square or circular or oval or any other shape.

Preferably, the dimensions and/or shapes of the plurality of identical sections or ROIs are pre-set. Alternatively, the dimensions and/or shapes of the plurality of identical sections or ROIs are variable and can in particular be adapted to scanned recognizable structures, preferably automatically by the computer of the medical or dental imaging system. The dimensions and/or shapes of the plurality of identical sections or ROIs may preferably depend on the variation of the at least one reconstruction parameter. The number of sections or ROIs per provisional panoramic image may preferably be defined by the number of frames, e.g. a section/ROI comprises a set or constant number of frame data set. Variable sections or ROIs advantageously allow for a more accurate calculation of the final panoramic image.

Preferably, if the provisional panoramic images are divided into identical sections or ROIs and at least some of the identical sections or ROIs of different provisional panoramic images represent a particular (same) recognizable structure, the section or ROI of the identical sections or ROIs representing the particular recognizable structure with the highest imaging quality, optionally in addition the frame data sets forming this section or ROI, and the provisional panoramic image comprising this section or ROI are determined. If there are a plurality of recognizable structures this procedure is preferably repeated for additional recognizable structures of this plurality of recognizable structures, in particular for a recognizable structure represented in other identical sections or ROIs (for which no recognizable structure with the highest imaging quality has been determined so far), so that finally for each plurality of identical sections or ROIs the section or ROI having a particular recognizable structure with the highest imaging quality and the provisional panoramic image comprising this section or ROI are determined.

Preferably, the provisional panoramic images can be divided into the plurality of sections or ROIs after calculating the provisional panoramic images from said plurality of frame data sets and before the scanning for recognizable structures. Then, the identical sections or ROIs of different provisional panoramic images are scanned for a particular recognizable structure and the section or ROI having the particular recognizable structure with the highest imaging quality is determined as described above.

Alternatively, the provisional panoramic images can be divided into the plurality of sections or ROIs after the scanning for recognizable structures. This allows for matching sections or ROIs to scanned recognizable structures, as described above, so that in particular the sections or ROIs of a provisional panoramic image may have different dimensions and/or shapes. Then again, the identical sections or ROIs of different provisional panoramic images are scanned for a particular recognizable structure and the section or ROI having the particular recognizable structure with the highest imaging quality is determined as described above.

As a result of these previous steps there is established a relation between sections or ROIs and/or frame data sets having recognizable structures with the highest imaging qualities and the respective provisional panoramic image having these sections, ROIs and/or frame data sets with recognizable structures with the highest imaging qualities. For example, and without any limitation to the figures or appellations mentioned, there may be established a relation such as: Highest quality of recognizable structure A in provisional panoramic image 3, section/ROI 2 and/or frame data sets 2.357-2.529;

B in provisional panoramic image 5, section/ROI 4 and/or frame data sets 4.101-4.237;

C in provisional panoramic image 2, section/ROI 1 and/or frame data sets 805-1.009;

D in provisional panoramic image 2, section/ROI 5 . . . .

Preferably, the established relation comprises information about each section or ROI of the plurality of sections or ROIs. For example, if each of the provisional panoramic images has been divided into five identical sections or ROIs, the established relation comprises five records, each record referring to one of the respective five sections or ROIs. Accordingly, the established relation preferably comprises information about all frame data sets forming the provisional panoramic images.

Based on said established relation, it is now possible to determine the variation of the at least one reconstruction parameter previously used for the calculation of the plurality of provisional panoramic images of those frame data sets and/or sections/ROIs having recognizable structures with the highest imaging quality, i.e. of those frame data sets and/or sections/ROIs comprised in the established relation. With respect to the sections or ROIs, in particular the variation of the at least one reconstruction parameter of those frame data sets forming the section or ROI of said identical sections or ROIs which has a recognizable structure with the highest imaging quality is determined.

Accordingly, through this step there is established a relation between a section/ROI of a plurality of identical sections/ROIs having the (recognizable structure with the) highest imaging quality and the variation of the at least one reconstruction parameter of this section/ROI or between frame data sets representing a recognizable structure having the highest imaging quality compared to identical frame data sets representing this recognizable structure of the different provisional panoramic images and the variation of the at least one reconstruction parameter of these frame data sets having the highest imaging quality.

Based on this relation, it is now possible to calculate, in particular with reference to the determined variation of the at least one reconstruction parameter, a final panoramic image data set representing a final panoramic image.

According to a first embodiment, the final panoramic image data set is calculated based on the plurality of captured frame data sets (i.e. the 'original' frame data sets) and the determined variation of the at least one reconstruction parameter of those frame data sets of the plurality of different provisional panoramic images having the recognizable structures with the highest imaging quality. Alternatively, if the different provisional panoramic images have been divided into sections or ROIs, the final panoramic image data set is calculated based on the plurality of captured frame data sets (i.e. the 'original' frame data sets) and the determined variation of the at least one reconstruction parameter of the frame data sets forming those respective sections/ROIs of the plurality of different provisional panoramic images which have the recognizable structures with the highest imaging quality.

According to both alternatives of the first embodiment, the final panoramic image data set is newly calculated from the plurality of captured ('original') frame data sets, which advantageously results in a final panoramic image data set and final panoramic image with a very high quality.

If the different provisional panoramic images have been divided into sections or ROIs, preferably the final panoramic image data set is calculated by using the variation of the at least one reconstruction parameter leading to the highest imaging quality of different provisional panoramic images (based on the established relation above), and in particular by bringing together these variations of the at least one reconstruction parameter of different provisional panoramic images to calculate or create the final panoramic image data set and final panoramic image.

This calculation is continued for each section or ROI, so that in the end the final panoramic image data set comprised of all sections or ROIs is obtained. Accordingly, the final panoramic image data set is composed of different sections/ROIs of different provisional panoramic images, each section/ROI having the highest quality (compared to the other identical sections/ROIs), in particular the highest quality of the geometry of anatomical structures. Thus, the obtained final panoramic image has improved representation of the geometry of anatomical structures.

If the different provisional panoramic images have not been divided into sections or ROIs, the same calculation is made with direct reference to the frame data sets representing the respective recognizable structures with the highest imaging qualities.

The final panoramic image data set is calculated by using the variation of the at least one reconstruction parameter of frame data sets representing a recognizable structure having the highest imaging quality of different provisional panoramic images, and in particular by bringing together these variations of the at least one reconstruction parameter of frame data sets of different provisional panoramic images to calculate or create the final panoramic image data set and final panoramic image.

This calculation is continued for all frame data sets, so that in the end the final panoramic image data set comprised of all frame data sets is obtained. Accordingly, the final panoramic image data set is composed of frame data sets of different provisional panoramic images having the highest quality (compared to the other identical frame data sets), in particular the highest quality of the geometry of anatomical structures. Thus, the obtained final panoramic image has improved representation of the geometry of anatomical structures.

According to a second embodiment, the final panoramic image data set is calculated by combining those frame data sets of the plurality of different provisional panoramic images having the recognizable structures with the highest imaging quality. Alternatively, the final panoramic image data set is calculated by combining those respective sections or ROIs of the plurality of different provisional panoramic images which have the recognizable structures with the highest imaging quality. This second embodiment advantageously provides the final panoramic image data set and thus the final panoramic image very quickly, since no new calculation based on the captured ('original') frame data sets is required.

Preferably, the frame data sets with the highest imaging quality or the sections/ROIs with the highest imaging quality are cut out and/or copied from their respective provisional panoramic images and joined to form the final panoramic image data set and final panoramic image.

According to a third embodiment, the final panoramic image data set is calculated based on one of the provisional panoramic images of the plurality of provisional panoramic images and the determined variation of the at least one reconstruction parameter of those frame data sets of the plurality of different provisional panoramic images having the recognizable structures with the highest imaging quality or of the frame data sets forming those respective sections or ROIs of the plurality of different provisional panoramic images which have the recognizable structures with the highest imaging quality. This third embodiment advantageously provides the final panoramic image data set and thus the final panoramic image quickly, because the number of required calculations to obtain the final panoramic image data set is reduced, since one of the provisional panoramic images is used as a basis for the final panoramic image.

The provisional panoramic image corresponding to the target position may preferably form the base for the final panoramic image data set.

If the provisional panoramic images have been divided into sections or ROIs and the provisional panoramic image which is used as basis for the final panoramic image data set comprises at least one section or ROI which represents a (first) recognizable structure with the highest imaging quality and at least one section or ROI which does not represent a (second, different) recognizable structure with the highest imaging quality, then preferably the at least one section or ROI which does not represent a recognizable structure with the highest imaging quality is replaced by the identical section or ROI of another provisional panoramic image representing the (second, different) recognizable structure with the highest imaging quality, while the at least one section or ROI which represents the (first) recognizable structure with the highest imaging quality remains.

Accordingly, if the provisional panoramic images have not been divided into sections or ROIs and the provisional panoramic image which is used as basis for the final panoramic image data set comprises frame data sets which represents a (first) recognizable structure with the highest imaging quality and frame data sets which do not represent a (second, different) recognizable structure with the highest imaging quality, then preferably the frame data sets which do not represent a recognizable structure with the highest imaging quality are replaced by the identical frame data sets of another provisional panoramic image representing the (second, different) recognizable structure with the highest imaging quality, while the frame data sets which represents the (first) recognizable structure with the highest imaging quality remain.

The replacement of the frame data sets or section/ROI which does/do not represent a recognizable structure with the highest imaging quality may be carried out by newly calculating theses frame data sets or this section/ROI from the plurality of captured ('original') frame data sets (forming this section/ROI) and the determined variation of the at least one reconstruction parameter of these frame data sets or this section/ROI representing the recognizable structure with the highest imaging quality as described for the first embodiment. Alternatively or in addition, the replacement may be carried out by cutting out and/or copying frame data sets with the highest imaging quality or a section/ROI with the highest imaging quality from their respective provisional panoramic images and adding it to the provisional panoramic image which is used as basis for the final panoramic image data set, similar to the second embodiment. Adding the cut out and/or copied frame data sets or section/ROI may either comprise superimpose the cut out and/or copied frame data sets or section/ROI over the identical frame data sets or section/ROI of the provisional panoramic image which is used as basis for the final panoramic image data set or cutting out or removing the identical frame data sets or section/ROI of the provisional panoramic image which is used as basis for the final panoramic image data set and inserting the cut out and/or copied frame data sets or section/ROI into the place where the identical frame data sets or section/ROI have/has been removed.

Preferably, the provisional panoramic image which is used as basis for the final panoramic image data set comprises a plurality of sections/ROIs and/or frame data sets representing recognizable structures with the highest imaging quality. This advantageously reduces the number of calculations to receive the final panoramic image data set.

Preferably, calculating the final panoramic image data set comprises scaling or further processing the final panoramic image data set. Further processing may comprise for example filtering, adjusting sharpness or levels of grey, noise reduction, in particular before displaying the final panoramic image.

Finally, the final panoramic image represented by the final panoramic image data set is displayed on a monitor or display. Preferably, the monitor or display is part of the medical or dental imaging system and/or communicatively connected to the medical or dental imaging system, in particular to the computer. Preferably, the monitor or display is communicatively connected to the computer, so that the final panoramic image data set can be transmitted to the monitor or display.

According to an embodiment a computer program product or computer-readable storage medium are provided which comprise instructions which, when executed by a computer, cause the computer to perform the computer implemented method described in this document. The computer program product or computer-readable storage medium are preferably provided in the computer of the medical or dental imaging system or x-ray device which have been described in the foregoing. The computer may be a local computer being a physical part of the medical or dental imaging system or a remote computer or Cloud computer, which is communicatively connected to the medical or dental imaging system, for example via Wi-Fi, an Internet connection or any other suitable communication link. The computer may comprise a controller, a memory, software, firmware, hardware and any other well-known components to be able to perform the computer implemented method described in this document.

According to an embodiment a medical or dental imaging system for generating an image of at least a part of the head of a patient is provided, the medical or dental imaging system comprising: a radiation source and a radiation detector which are configured to move about a patient to capture a plurality of frame data sets, and a computer which is operatively connected to the radiation detector to receive the plurality of frame data sets and which comprises a computer program product or computer-readable storage medium as described above to perform the computer implemented method described in this document.

The medical or dental imaging system comprises preferably a computer as described in the forgoing. The medical or dental imaging system comprises preferably an x-ray device and/or an x-ray source and an x-ray detector. The medical or dental imaging system comprises preferably one or more additional components as described above, for example a supporting structure, a rotation unit rotatably, a chin rest and/or bite block, a display or monitor.

These and other embodiments will be described below with reference to the following drawings.

DETAILED DESCRIPTION

Figures 1, 2:
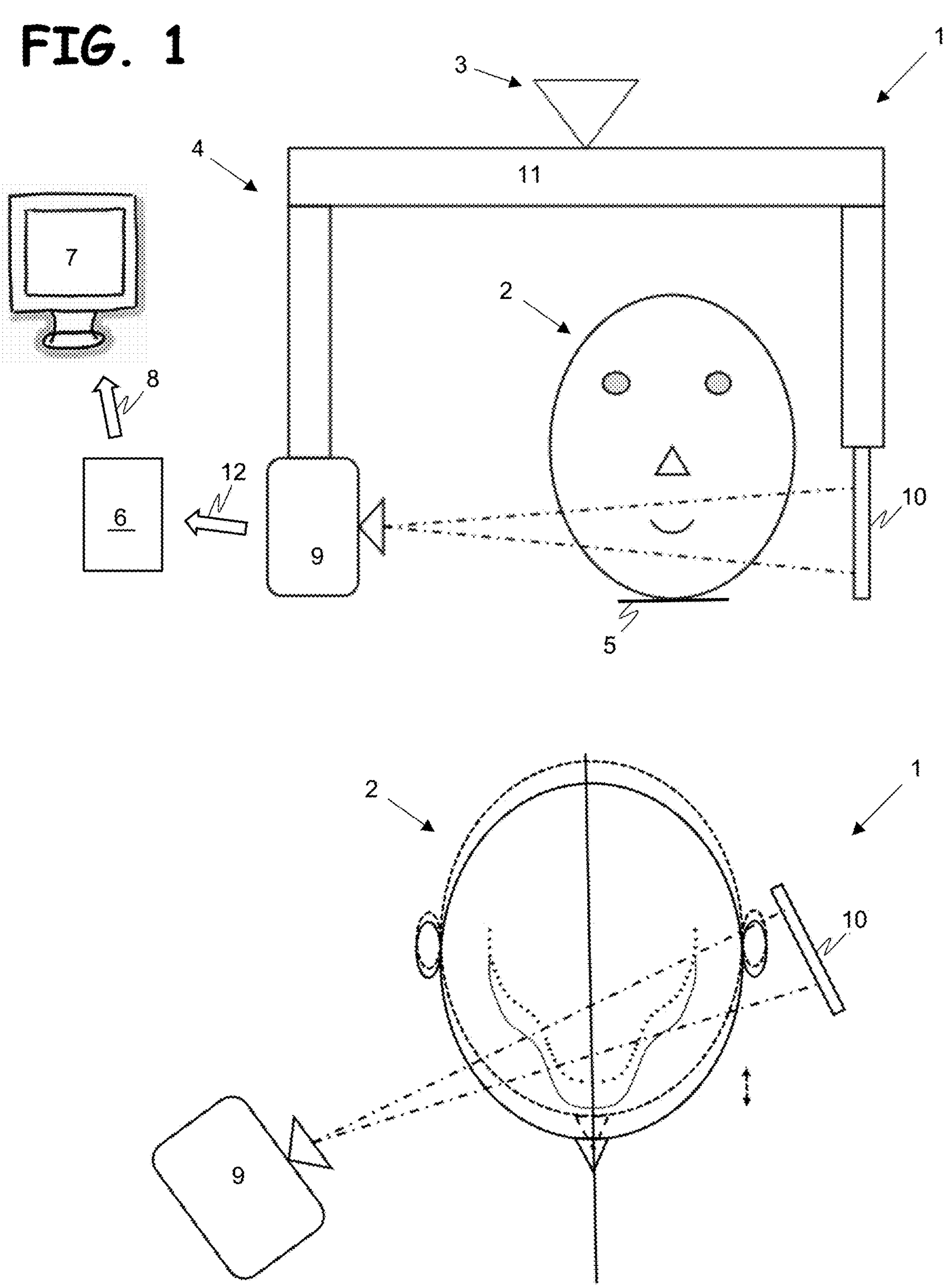
FIG. 1 shows a schematic representation of a medical or dental imaging system with a head of a patient.
FIG. 2 schematically shows a medical or dental imaging system with a head of a patient in a target position and in a deviated position.

FIG. 1 shows a medical or dental imaging system 1, in particular an x-ray imaging system, for generating a 2D panoramic image of at least a part of the head 2 of a patient. The medical or dental imaging system 1 comprises a frame or supporting structure 3 (only a portion of the frame 3 is depicted), a rotation unit 4 rotatably coupled to the frame 3, a chin rest 5 and a computer 6 configured to perform the image processing method described in this document. In particular the computer 6 comprises software, programs and/or a computer-readable storage medium comprising instructions which, when executed by a computer, cause the computer to perform the method described in this document. A monitor or display 7 is communicatively (see arrow 8) connected to the computer 6 to receive imaging data to display the 2D panoramic image.

Rotation unit 4 comprises a radiation or x-ray source 9 for the emission of radiation, in particular x-rays, towards at least a part of the head 2 of the patient to be imaged and a radiation, in particular x-ray, detector 10 which is configured to receive at least a portion of the radiation emitted by the radiation source 9, in particular the x-rays which have penetrated the head part 2 to be imaged. The rotation unit 4 comprises a cantilever or a rotating arm 11 having two opposing end sections, wherein the radiation source 9 is attached to one of these respective end sections and the radiation detector 10 is attached to the other of these respective end sections.

Rotation unit 4, in particular rotating arm 11 is rotatably coupled to frame 3 so that rotation unit 4 with radiation source 9 and the radiation detector 10 is configured to rotate around head 2 of the patient. During rotation radiation source 9 and radiation detector 10 take up a plurality of different positions relative to head 2 and capture a plurality of frame data sets 13 (single images) of the at least one part of head 2 at said different positions, see also FIGS. 3 and 4, step (i). These frame data sets 13 are transmitted to computer 6 (see arrow 12) and processed, in particular according to the method described in this document, by computer 6.

FIG. 2 shows medical or dental imaging system 1 with head 2 of a patient being in two different positions: the head displayed in continuous lines is in the target position, while the head represented in dashed lines is shifted and thus not positioned in the target position. If head 2 is in the target position computer 6 can calculate an optimal final 2D panoramic image, since calculation rules, metrics, reconstruction parameters and/or algorithms for the calculation of the final 2D panoramic image are configured for the target position. As described above in detail, often head 2 of the patient is not in the target, but in a shifted and/or rotated position and thus the quality of the captured frame data sets 13 and in particular of the final 2D panoramic image is poor, since calculation rules, metrics, reconstruction parameters and/or algorithms for the calculation of the final 2D panoramic image are not adapted to calculate a final 2D panoramic image of a head 2 being out of the target position. Poor quality of the final 2D panoramic image in particular shows in poor representation of the geometry of at least some of the anatomical structures on the final 2D panoramic image, like geometrical distortions, wrong proportions etc. of anatomical structures.

Figure 3:
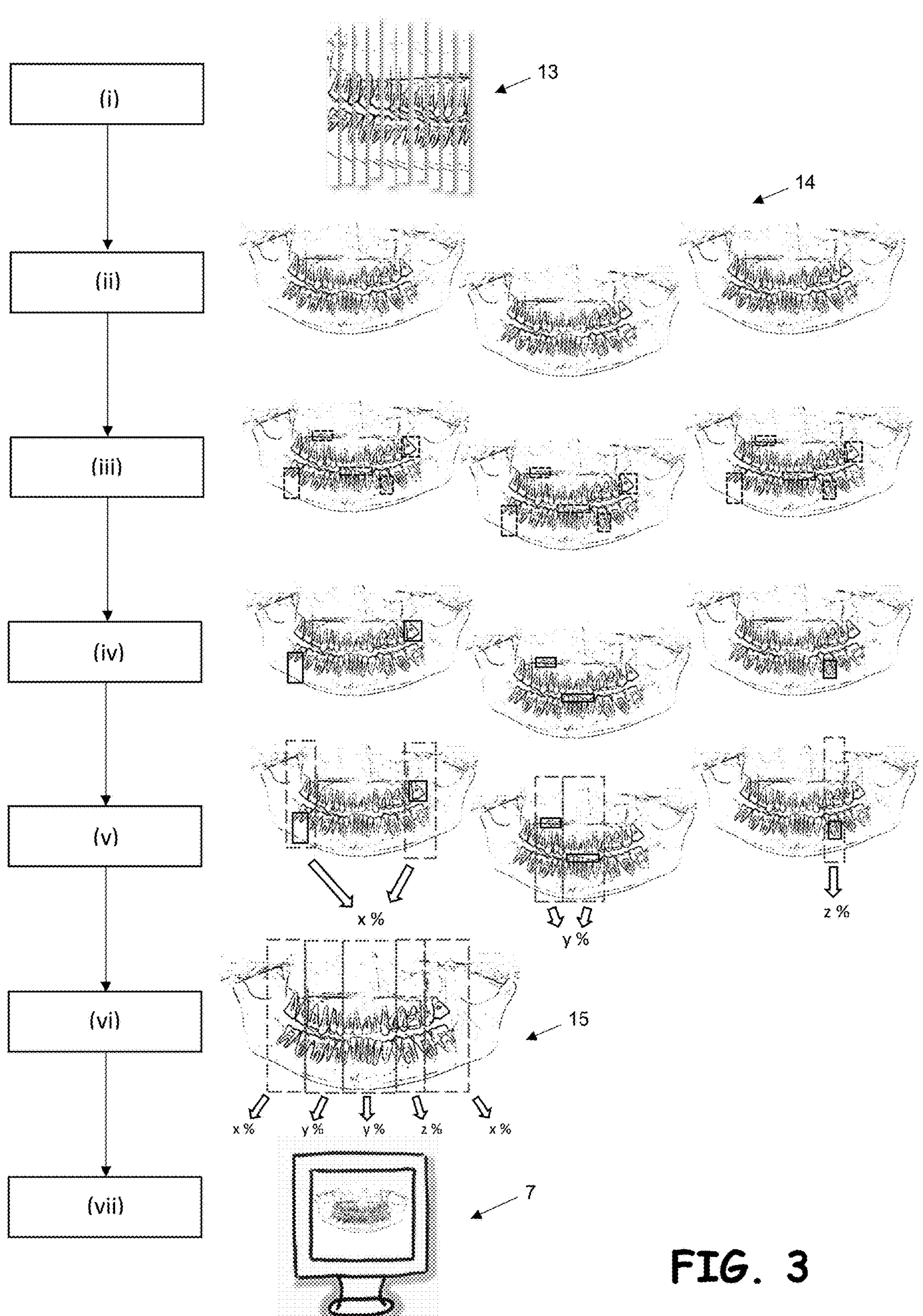
FIG. 3 shows steps of an image processing method to provide a final panoramic image of at least a portion of a head with improved representation of the geometry of anatomical structures of the head.
Figure 4:
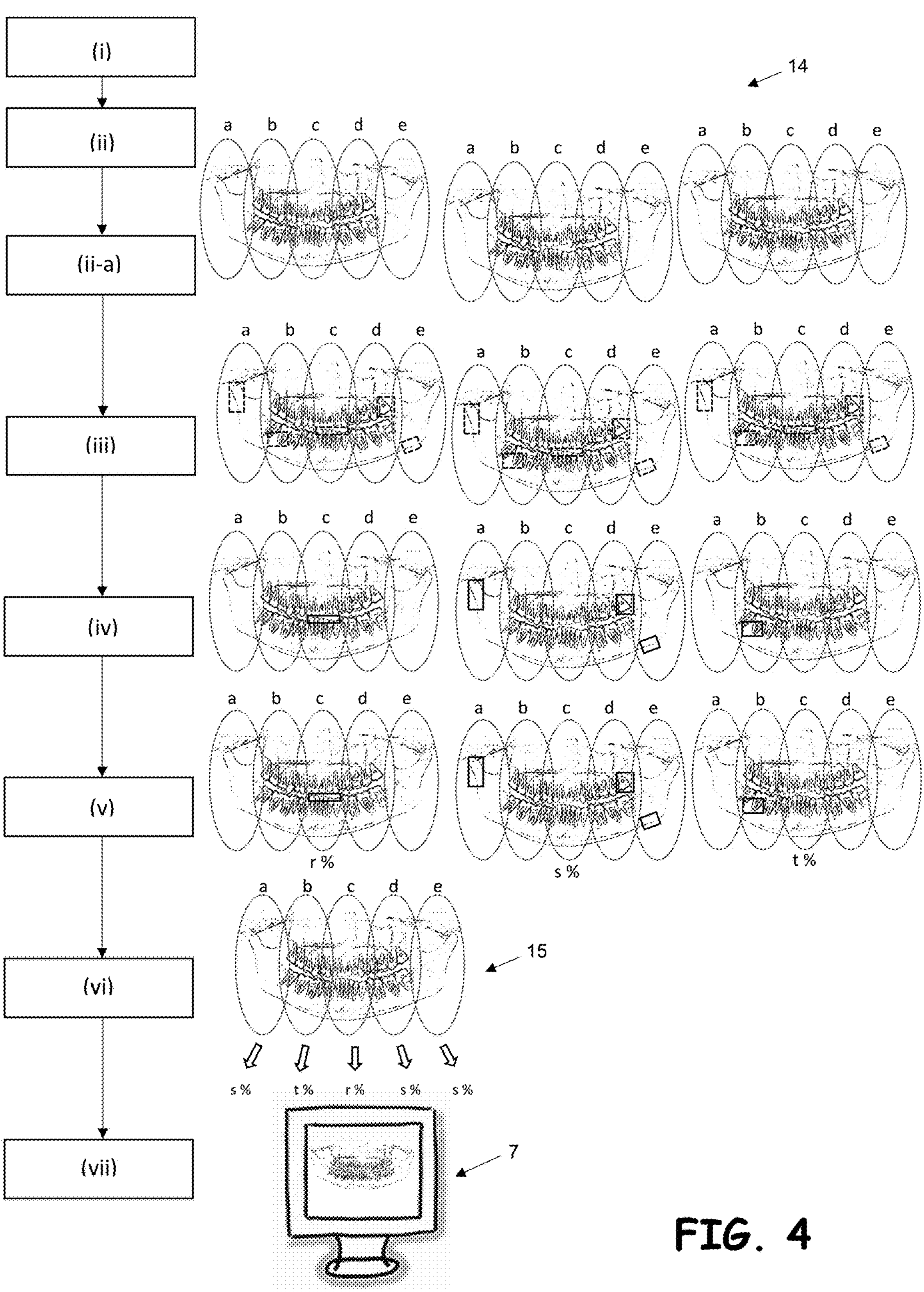
FIG. 4 shows steps of an image processing method having an additional step compared to the method of FIG. 3 to provide a final panoramic image of at least a portion of a head with improved representation of the geometry of anatomical structures of the head.

The methods shown in FIGS. 3 and 4 are configured to correct the consequences of head 2 being out of the target position and finally provide final 2D panoramic images with better or corrected representation of the geometry of at least some of the anatomical structures. Since steps (i) and (ii) of both methods shown in FIGS. 3 and 4 are identical, the description of these steps (i) and (ii) applies to FIGS. 3 and 4.

According to step (i) a plurality of frame data sets 13 is captured by the medical or dental imaging system 1, in particular by radiation source 9 and a radiation detector 10 while moving about the head 2. Each frame data sets 13 usually has an elongate or stripe shape. In particular in FIG. 3, for clarity only a very small number of frame data sets 13 is shown, while in reality the number of captured frame data sets 13 may comprise hundreds or some thousands. The plurality of frame data sets 13 is transmitted wired or wirelessly to computer 6 for further processing.

In step (ii) calculation rules, metrics and/or algorithms of computer 6 calculate a plurality of different provisional panoramic images 14 from the plurality of frame data sets 13. In FIGS. 3 and 4 again for clarity only three provisional panoramic images 14 are shown, while in practice a different number of provisional panoramic images 14 may be calculated, for example between 4-20 or more. Generally, the captured frame data sets 13 are combined or arranged in an overlapping manner and in the order they have been captured to receive a provisional panoramic image 14. The calculated provisional panoramic images of this plurality of provisional panoramic images 14 differ from one another due to variations of the at least one reconstruction parameter during calculation. The at least one reconstruction parameter may comprise for example at least one of: a rate of overlap of the frame data sets; a rate of scaling of the frame data sets; a pixel shift. This variation is comparatively small, for example it comprises a variation in the range of a portion of a pixel or one or few pixels. As a result of the variation of the at least one reconstruction parameter provisional panoramic images 14 differ at least in the geometrical representation of the anatomical or artificial structures they represented. This means in particular, that due to the variation of the at least one reconstruction parameter an identical anatomical or artificial structure represented on different provisional panoramic images 14 may be represented in higher quality (in particular with respect to the quality of geometrical representation) on one of these provisional panoramic images 14 and/or in lower quality (of geometrical representation) on another provisional panoramic image 14.

In the following the embodiment according to FIG. 3 is described.

In step (iii) the plurality of provisional panoramic images 14 is scanned for recognizable structures, which are marked in FIG. 3 by dashed lines. These recognizable structures may comprise anatomical and/or artificial structures or portions thereof, for example with reference to FIG. 3 and starting from the left: a portion of a root of a molar; a portion of a palate; edges of several incisors; a portion of a root of another molar; an entire tooth (molar). As can be seen in FIG. 3 all three depicted provisional panoramic images 14 represent these five exemplary structures, but as already explained above, due to the variation of the at least one reconstruction parameter an identical structure may be represented in different quality on different provisional panoramic images 14. Further it is also possible, that at least one structure is not represented on at least one of the provisional panoramic images 14.

According to step (iv) the imaging quality of the structures recognized in step (iii) is determined. The imaging quality is preferably defined by geometrical parameters, such as spatial positioning, proportions or dimensions of structures represented on the provisional panoramic images. Further, the imaging qualities of identical structures represented on different provisional panoramic images 14 are compared and the provisional panoramic image 14 and the frame data sets 13 representing the structure having the highest imaging quality (compared to identical structures on other provisional panoramic images 14) are determined. This is repeated for a plurality or all of the structures recognized in step (iii). Referring to the three provisional panoramic images 14 shown in FIG. 3, step (iv), one can exemplarily see that, starting from the left, the first provisional panoramic image comprises two structures having the highest quality (compared to the respective identical structures on the two other provisional panoramic images), namely the portion of a root of a molar on the left and the entire tooth (molar), the second, central provisional panoramic image also comprises two structures having the highest quality (compared to identical respective structures on the two other provisional panoramic images), namely the portion of a palate and the edges of several incisors, while the third provisional panoramic image comprises one structure having the highest quality (compared to the respective identical structure on the two other provisional panoramic images), namely the portion of a root of another molar on the right. Each of these structures having the highest quality is marked in FIG. 3, step (iv), in the respective provisional panoramic image 14 by a continuous line.

According to step (v), the variations of the at least one reconstruction parameter used in step (ii) for the calculation of the plurality of provisional panoramic images 14 of those frame data sets 13 which have recognized structures with the highest imaging quality are determined. As can be seen exemplarily with respect to the three provisional panoramic images 14 shown in FIG. 3, step (v), again starting from the left, the first provisional panoramic image was calculated with a variation of the at least one reconstruction parameter of the frame data sets 13 of x % and thus the two recognized structures of this first provisional panoramic image (i.e. the portion of a root of a molar on the left and the entire tooth) and preferably any other structure comprised on the frame data sets 13 which represent these two structures and/or generally the frame data sets 13 which represent these two structures and which are marked through dashed lines have the highest quality when calculated with a variation of the at least one reconstruction parameter of the frame data sets 13 of x %; the second, central provisional panoramic image was calculated with a variation of the at least one reconstruction parameter of the frame data sets 13 of y % and thus the two recognized structures of this second provisional panoramic image (i.e. the portion of a palate and the edges of several incisors) and preferably any other structure comprised on the frame data sets 13 which represent these two structures and/or generally the frame data sets 13 which represent these two structures and which are marked through dashed lines have the highest quality when calculated with a variation of the at least one reconstruction parameter of the frame data sets 13 of y %; and the third provisional panoramic image was calculated with a variation of the at least one reconstruction parameter of the frame data sets 13 of z % and thus the recognized structure of this third provisional panoramic image (i.e. the portion of a root of another molar on the right) and preferably any other structure comprised on the frame data sets 13 which represent this molar and/or generally the frame data sets 13 which represent this molar and which is marked through dashed lines have the highest quality when calculated with a variation of the at least one reconstruction parameter of the frame data sets 13 of z %; wherein x, y and z represent different variations of the at least one reconstruction parameter and different numerical values, i.e. $x \neq y \neq z$.

Accordingly, based on these previous steps, in particular step (v), it is now known which variation of the at least one reconstruction parameter the calculation rules, metrics and/or algorithms of computer 6 have to apply to particular frame data sets to create or calculate a final panoramic image data set representing a final panoramic image 15 with highest quality, i.e., improved representation of the geometry of anatomical structures, see step (vi) of FIG. 3.

Preferably, the final panoramic image data set is newly calculated based on the plurality of captured frame data sets (i.e., the 'original' frame data sets 13) and the determined variations of the at least one reconstruction parameter, while other ways to create the final panoramic image data set and the final panoramic image 15 are also possible and have been described above. With respect to step (vi) of FIG. 3 the final panoramic image 15 comprises five portions, wherein, starting from the left, the first portion comprising the frame data sets 13 which represent the portion of a root of a molar on the left has been calculated with reference to the left provisional panoramic image in step (v) with a variation of the at least one reconstruction parameter of the frame data sets 13 of x %; the following second portion comprising the frame data sets 13 which represent the portion of a palate has been calculated with reference to the central provisional panoramic image in step (v) with a variation of the at least one reconstruction parameter of the frame data sets 13 of y %; also the following central, third portion comprising the frame data sets 13 which represent the edges of several incisors has been calculated with reference to the central provisional panoramic image in step (v) with a variation of the at least one reconstruction parameter of the frame data sets 13 of y %; the following fourth portion comprising the frame data sets 13 which represent the portion of a root of another molar on the right has been calculated with reference to the provisional panoramic image on the right in step (v) with a variation of the at least one reconstruction parameter of the frame data sets 13 of z %; and the final fifth portion comprising the frame data sets 13 which represent the entire tooth has again been calculated with reference to the left provisional panoramic image in step (v) with a variation of the at least one reconstruction parameter of the frame data sets 13 of x %.

Finally, according to step (vii) the final panoramic image 15 represented by the final panoramic image data set created in step (vi) is displayed on a display or monitor 7.

In the following the embodiment according to FIG. 4 is described.

Following steps (i) and (ii) which have already been described above the calculated provisional panoramic images 14 are divided into a plurality of sections or regions of interest (ROIs), wherein the plurality of sections/ROIs is identical for each provisional panoramic image 14, see FIG. 4, step (ii-a). Exemplarily, each of the three provisional panoramic images 14 is divided into five identical sections/ROIs a-e.

In following step (iii) the plurality of provisional panoramic images 14, in particular each of the sections/ROIs a-e of each provisional panoramic images 14, is scanned for recognizable structures, which are marked in FIG. 4 by dashed lines. These recognizable structures may comprise anatomical and/or artificial structures or portions thereof, wherein for example with reference to FIG. 4: the recognizable structure in section/ROI a comprises a portion of a temporomandibular joint; the recognizable structure in section/ROI b comprises portions of several tooth roots; the recognizable structure in section/ROI c comprises edges of several incisors; the recognizable structure in section/ROI d comprises an entire tooth (molar); and the recognizable structure in section/ROI e comprises a portion of the lower jaw. As can be seen in FIG. 4 all three depicted provisional panoramic images 14 represent these five exemplary structures, but as already explained above, due to the variation of the at least one reconstruction parameter an identical structure may be represented in different quality (in particular with respect to the quality of geometrical representation) on different provisional panoramic images 14. Further it is also possible, that at least one structure is not represented on at least one of the provisional panoramic images 14.

According to step (iv) the imaging quality of the structures recognized in step (iii) is determined. The imaging quality is preferably defined by geometrical parameters, such as spatial positioning, proportions or dimensions of structures represented on the provisional panoramic images. Further, the imaging qualities of identical structures represented in identical sections/ROIs a-e in different provisional panoramic images 14 are compared and the provisional panoramic image 14 and the section/ROI a-e, preferably also the frame data sets 13, representing the structure having the highest imaging quality (compared to identical structures in identical sections/ROIs a-e in other provisional panoramic images 14) are determined. This is done at least once for every section/ROI a-e, so that every section/ROI a-e comprises in one of the provisional panoramic images 14 a structure having the highest imaging quality. Referring to the three provisional panoramic images 14 shown in FIG. 4, step (iv), one can exemplarily see that sections/ROIs a, d and e comprise respective structures having the highest imaging quality (compared to the respective identical structures on the two other provisional panoramic images) in the central provisional panoramic image 14, section/ROI b comprises the structure having the highest imaging quality (compared to the respective identical structure on the two other provisional panoramic images) in the right provisional panoramic image 14, and section/ROI c comprises the structure having the highest imaging quality (compared to the respective identical structure on the two other provisional panoramic images) in the left provisional panoramic image 14. Each of these structures having the highest quality is marked in FIG. 4, step (iv), in the respective provisional panoramic image 14 by a continuous line.

According to step (v), the variations of the at least one reconstruction parameter used in step (ii) for the calculation of the plurality of provisional panoramic images 14 of the frame data sets 13 of those sections/ROIs a-e which have recognized structures with the highest imaging quality are determined. As can be seen exemplarily with respect to the three provisional panoramic images 14 shown in FIG. 4, step (v), beginning from the left, the first provisional panoramic image was calculated with a variation of the at least one reconstruction parameter of the frame data sets 13 of r % and thus the frame data sets 13 of section/ROI c (having the recognized structure with the highest quality of all sections/ROIs c of the three provisional panoramic images 14) yield the highest quality when calculated with a variation of the at least one reconstruction parameter of the frame data sets 13 of r %; the second, central provisional panoramic image was calculated with a variation of the at least one reconstruction parameter of the frame data sets 13 of s % and thus the frame data sets 13 of sections/ROIs a, d and e (having the respective recognized structures with the highest quality of the respective sections/ROIs a, d, e of the three provisional panoramic images 14) yield the highest quality when calculated with a variation of the at least one reconstruction parameter of the frame data sets 13 of s %; and the third provisional panoramic image was calculated with a variation of the at least one reconstruction parameter of the frame data sets 13 of t % and thus the frame data sets 13 of section/ROI b (having the recognized structure with the highest quality of all sections/ROIs b of the three provisional panoramic images 14) yield the highest quality when calculated with a variation of the at least one reconstruction parameter of the frame data sets 13 of t %.

Accordingly, based on these previous steps, in particular step (v), it is now known which variations of the at least one reconstruction parameter the calculation rules, metrics and/or algorithms of computer 6 have to apply to the frame data sets of sections/ROIs a-e to create or calculate a final panoramic image data set representing a final panoramic image 15 with highest quality, i.e. improved representation of the geometry of anatomical structures, see step (vi) of FIG. 4.

Preferably, the final panoramic image data set is newly calculated based on the plurality of captured frame data sets (i.e., the 'original' frame data sets 13) and the determined variations of the at least one reconstruction parameter of sections/ROIs a-e, while other ways to create the final panoramic image data set and the final panoramic image 15 are also possible and have been described above. With respect to step (vi) of FIG. 4 the final panoramic image 15 comprises the five sections/ROIs a-e, wherein, the frame data sets 13 of section/ROI a have been calculated with reference to the central provisional panoramic image in step (v) with a variation of the at least one reconstruction parameter of the frame data sets 13 of s %; the frame data sets 13 of section/ROI b have been calculated with reference to the right provisional panoramic image in step (v) with a variation of the at least one reconstruction parameter of the frame data sets 13 of t %; the frame data sets 13 of section/ROI c have been calculated with reference to the left provisional panoramic image in step (v) with a variation of the at least one reconstruction parameter of the frame data sets 13 of r %; and the frame data sets 13 of sections/ROIs d and e have been calculated with reference to the central provisional panoramic image in step (v) with a variation of the at least one reconstruction parameter of the frame data sets 13 of s %; wherein r, s and t represent different variations of the at least one reconstruction parameter and different numerical values, i.e. $r \neq s \neq t$.

Finally, according to step (vii) the final panoramic image 15 represented by the final panoramic image data set created in step (vi) is displayed on a display or monitor 7.

The embodiments of the methods shown in FIGS. 3 and 4 only represent the basic steps of said methods, so that additional steps, in particular as described herein, may be added. Also, the number of frame data sets 13, sections or ROIs a-e, provisional panoramic images 14 and any other figures, measures or dimensions mentioned or referred to with respect to FIGS. 3 and 4 are only exemplary, so that the image processing methods described herein are not limited to these figures, measures or dimensions.

The embodiments described or shown, in particular, serve to depict the invention. The characteristics, disclosed in an embodiment, are therefore not limited to that embodiment, but can rather be combined individually or together with one or more characteristics of one of the other embodiments.

What is claimed is:

1. An image processing method to provide a final panoramic image of at least a portion of a head, wherein the image processing method comprises:

i. providing a single frame data set comprising a plurality of frames captured by a medical or dental imaging system having a radiation source and a radiation detector which move about a patient on a single trajectory while taking the plurality of frames;

ii. simulating different geometric positions of the portion of the head by calculating by a computer from said single frame data set, and before step iv., at least a first and second provisional panoramic image, wherein for the calculation of the first provisional panoramic image a first reconstruction parameter or value of a reconstruction parameter is applied to the frames of the single frame data set, and for the calculation of the second provisional panoramic image a second reconstruction parameter or value of a reconstruction parameter is applied to the frames of the single frame data set, wherein the second reconstruction parameter or value of a reconstruction parameter is different than the first reconstruction parameter or value of a reconstruction parameter, so that the first calculated provisional panoramic image differs from the second calculated provisional panoramic image;

iii. scanning the first and second provisional panoramic images for recognizable structures;

iv. determining imaging quality of the recognizable structures, comparing the imaging quality of identical recognizable structures of the first and second provisional panoramic images and selecting the recognizable structure of identical recognizable structures of the first or second provisional panoramic image having the highest imaging quality;

v. determining variation of the first or second reconstruction parameter or value of the reconstruction parameter used in step (ii) for calculation of the first and second provisional panoramic images of those frames which have the selected recognizable structures with the highest imaging quality;

vi. calculating by the computer with reference to the determined variation of the first or second reconstruction parameter or value of the reconstruction parameter of step (v) a final panoramic image data set representing a final panoramic image;

vii. displaying the final panoramic image represented by the final panoramic image data set with improved representation of the geometry of anatomical structures of the portion of the head, wherein the improved representation of the geometry comprises at least one of: correction of a translation to the left or right relative to the radiation detector; correction of a translation up or down relative to the radiation detector; or a combination thereof.

2. The method according to claim 1, wherein the variation of the first or second reconstruction parameter or value of the reconstruction parameter in step (ii) depends on the dimension of the portion of the head to be imaged.

3. The method according to claim 1, wherein the variation of the first or second reconstruction parameter or value of the reconstruction parameter in step (ii) is pre-set.

4. The method according to claim 1, wherein determining the imaging quality in step (iv) comprises image data processing of the frames comprising recognizable structures.

5. The method according to claim 4, wherein image data processing comprises at least one of: frequency analysis; grey value distribution analysis; brightness distribution analysis.

6. The method according to claim 1, wherein the first or second reconstruction parameter comprises at least one of: a rate of overlap of the frames; a rate of scaling of the frames; a pixel shift.

7. The method according to claim 1, wherein the first and second provisional panoramic images are divided into a plurality of sections or regions of interest, wherein the plurality of sections or regions of interest is identical for the first and second provisional panoramic images.

8. The method according to claim 7, wherein step (v) further comprises that the imaging quality of a recognizable structure of identical sections or regions of interest of the first and second provisional panoramic images is determined and the variation of the first or second reconstruction parameter or value of the reconstruction parameter of those frames forming the section or region of interest of said identical sections or regions of interest which has a recognizable structure with the highest imaging quality is determined.

9. The method according to claim 1, wherein in step (vi) the final panoramic image data set is calculated based on the plurality of frames captured in step (i) and the determined variation of the first or second reconstruction parameter or value of the reconstruction parameter of those frames of the first or second provisional panoramic image having the selected recognizable structures with the highest imaging quality.

10. The method according to claim 1, wherein in step (vi) the final panoramic image data set is calculated by combining those frames of the first and second provisional panoramic images having the selected recognizable structures with the highest imaging quality.

11. The method according to claim 1, wherein in step (vi) the final panoramic image data set is calculated based on one of the first or the second provisional panoramic image and the determined variation of the first or the second reconstruction parameter or value of the reconstruction parameter of those frames of the first or the second provisional panoramic image having the selected recognizable structures with the highest imaging quality.

12. The method according to claim 1, wherein calculating the final panoramic image data set comprises scaling the final panoramic image data set.

13. The method according to claim 1, wherein the recognizable structure in step (iii) comprises at least a portion of an anatomical structure or of an artificial structure.

14. A non-transitory computer-readable storage medium comprising instructions which, when executed by a computer, cause the computer to:

provide a single frame data set comprising a plurality of frames captured by a medical or dental imaging system having a radiation source and a radiation detector which move about a patient on a single trajectory while taking the frame data set;

calculate from said plurality of frames a plurality of provisional panoramic images by applying at least one different reconstruction parameter or at least one different value of a reconstruction parameter to the plurality of frames for every provisional panoramic image to be calculated, so that each calculated provisional panoramic image differs from another calculated provisional panoramic image;

scan the provisional panoramic images of said plurality of provisional panoramic images for recognizable structures;

determine imaging quality of the recognizable structures, compare the imaging quality of identical recognizable structures of different provisional panoramic images and select the recognizable structure of identical recognizable structures of different provisional panoramic images having the highest imaging quality;

determine variation of the at least one reconstruction parameter or value of the reconstruction parameter for calculation of the plurality of provisional panoramic images of those frames which have selected recognizable structures with the highest imaging quality; and calculate with reference to the determined variation of the at least one reconstruction parameter or value of the reconstruction parameter a final panoramic image data set representing a final panoramic image; and display the final panoramic image represented by the final panoramic image data set with improved representation of the geometry of anatomical structures of the portion of the head, wherein the improved representation of the geometry comprises at least one of: correction of a translation to the left or right relative to the radiation detector; correction of a translation up or down relative to the radiation detector; or a combination thereof.

15. A medical or dental imaging system for generating an image of at least a part of the head of a patient, comprising:

a radiation source and a radiation detector which are configured to move about a patient to capture a plurality of frames, and a computer which is operatively connected to the radiation detector to receive the plurality of frames and which is programmed to:

receive the plurality of frames captured by the radiation source and the radiation detector;

calculate from said plurality of frames a plurality of provisional panoramic images by applying at least one different reconstruction parameter or at least one different value of a reconstruction parameter to the plurality of frames for every provisional panoramic image to be calculated, so that each calculated provisional panoramic image differs from another calculated provisional panoramic image;

scan the provisional panoramic images of said plurality of provisional panoramic images for recognizable structures;

determine imaging quality of the recognizable structures, compare the imaging quality of identical recognizable structures of different provisional panoramic images, and select the recognizable structure of identical recognizable structures of different provisional panoramic images having the highest imaging quality;

determine variation of the at least one reconstruction parameter or value of the reconstruction parameter for calculation of the plurality of provisional panoramic images of those frames which have selected recognizable structures with the highest imaging quality;

calculate with reference to the determined variation of the at least one reconstruction parameter or value of the reconstruction parameter a final panoramic image data set representing a final panoramic image; and display the final panoramic image represented by the final panoramic image data set with improved representation of the geometry of anatomical structures of the portion of the head, wherein the improved representation of the geometry comprises at least one of: correction of a translation to the left or right relative to the radiation detector; correction of a translation up or down relative to the radiation detector; or a combination thereof.

16. The medical or dental imaging system according to claim 15, wherein the radiation source comprises an X-ray radiation source.

17. The method according to claim 8, wherein in step (vi) the final panoramic image data set is calculated based on the plurality of frames captured in step (i) and the determined variation of the first or second reconstruction parameter or value of the reconstruction parameter of the frames forming those respective sections or regions of interest of the first or second provisional panoramic image which have the selected recognizable structures with the highest imaging quality.

18. The method according to claim 8, wherein in step (vi) the final panoramic image data set is calculated by combining those respective sections or regions of interest of the first or second provisional panoramic image which have the selected recognizable structures with the highest imaging quality.

19. The method according to claim 8, wherein in step (vi) the final panoramic image data set is calculated based on the first or second provisional panoramic image and the determined variation of the first or second reconstruction parameter or value of the reconstruction parameter of the frames forming those respective sections or regions of interest of the first or second provisional panoramic image which have the selected recognizable structures with the highest imaging quality.

* * * * *